United States Patent [19]
Triano et al.

[11] Patent Number: 5,994,272
[45] Date of Patent: Nov. 30, 1999

[54] METHOD FOR INHIBITION OF HEAD FORMATION IN LETTUCE

[75] Inventors: Steven R. Triano, Prunedale; David M. Williams, Salinas, both of Calif.

[73] Assignee: Fresh Express Incorporated, Salinas, Calif.

[21] Appl. No.: 09/060,271

[22] Filed: Apr. 14, 1998

[51] Int. Cl.$^6$ .................................................. A01N 57/02
[52] U.S. Cl. ............................................................ 504/208
[58] Field of Search ............................................. 504/208

[56] References Cited

U.S. PATENT DOCUMENTS

| | | |
|---|---|---|
| 2,927,014 | 3/1960 | Goyette ........................................ 71/2.3 |
| 3,223,514 | 12/1965 | Gradsten ...................................... 71/2.3 |
| 3,531,549 | 9/1970 | Randall ....................................... 260/953 |
| 3,551,528 | 12/1970 | Randall ....................................... 260/928 |
| 3,879,188 | 4/1975 | Fritz et al. .................................... 71/86 |
| 4,240,819 | 12/1980 | Fritz et al. .................................... 71/76 |

*Primary Examiner*—S. Mark Clardy
*Attorney, Agent, or Firm*—Townsend and Townsend and Crew LLP

[57] ABSTRACT

This invention relates to the use of catechol or substituted catechol half esters of beta-haloethylphosphonic acid to inhibit head formation in lettuce. Increased pigmentation of the head leaves is achieved as a result of the application.

13 Claims, 2 Drawing Sheets

TREATED                    UNTREATED

TREATED  UNTREATED

TREATED

METHOD FOR INHIBITION OF HEAD FORMATION IN LETTUCE

CROSS-REFERENCE TO RELATED APPLICATIONS

Not applicable.

FEDERALLY SPONSORED RESEARCH OR DEVELOPMENT

Not applicable.

BACKGROUND OF THE INVENTION

This invention relates to the use of catechol or substituted catechol half esters of beta-haloethylphosphonic acid to inhibit head formation in lettuce.

Commercially important varieties of crisphead lettuce (*Lactuca sativa*) form heads, as they mature. Heads occur when the leaves curve over the center of the plant and fold over on each other tightly such that the exposure of the interior leaf tissue to sunlight is inhibited. Typically, these leaves are not well-pigmented and lack an abundance of chlorophyll in comparison with leaves that have been exposed to the sun. Though consumers enjoy the crisp nature of head lettuce, the lettuce lacks another highly valued consumer trait, darker green pigmentation, with a resulting higher β-carotene content.

Some phosphonate compounds have found use in the agricultural art, for example, for herbicidal purposes as described in U.S. Pat. Nos. 2,927,014 and 3,223,514. Compound 2-chloroethylphosphonic acid has been described in U.S. Pat. No. 4,240,819 to be useful in inhibiting plant growth. It is currently marketed for use in tomatoes, cherries, grapes, apples, walnuts, peppers, blackberries and cantaloupes and is advocated for the use of promoting early coloration and maturity of tomatoes, grapes, apples and pears. In the case of cherries, walnuts and apples, it loosens the fruit for earlier, more efficient harvest. The compound promotes fruit abscission in cantaloupes and accelerates ripening and loosening of blackberries.

SUMMARY OF THE INVENTION

This invention provides a method for increasing the green pigmentation of head lettuce leaves and increasing the nutritional content while retaining the crisp leaf quality of these varieties. We have discovered quite surprisingly that catechol or substituted catechol half esters of beta-haloethylphosphonic acids such as 2-chloroethylphosphonic acid have the effect of inhibiting head formation in lettuce by causing a vertical orientation of the leaves such that leaves usually found in the head are exposed to the sun. This permits a highly desirable greater degree of green pigmentation of the leaves and increased nutrition.

More particularly, the invention is a method for inhibiting head formation in a head-forming *Lactuca sativa* plant which comprises applying a catechol or substituted catechol half ester of beta-haloethylphosphonic acid to the plant after leaf formation. Such head forming lettuce plants include crisphead lettuce and butterhead lettuce. Preferably the beta-haloethylphosphonic acid is applied to a crisphead plant after about 15 to 20 leaves have formed on the plant. The beta-haloethylphosphonic acid is applied preferably in a soluble form by spray application at a rate of 50 to 3,000 mls per acre. Head lettuce varieties of *Lactuca sativa* plants treated with the formulations described herein are also claimed.

DESCRIPTION OF THE PREFERRED EMBODIMENT

Figure 1:
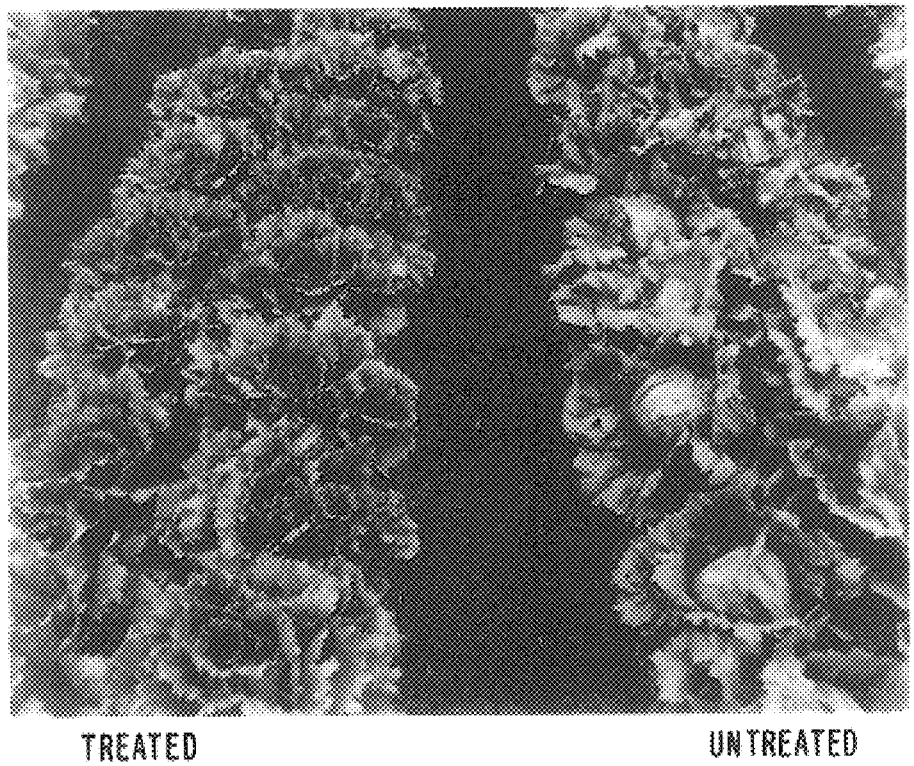
FIG. 1 illustrates two rows of crisphead lettuce. The row on the left was treated with a water base preparation of 2-chloroethylphosphonic acid. The row on the right was a control and was not treated. These plants are ready for harvest.
Figure 2:
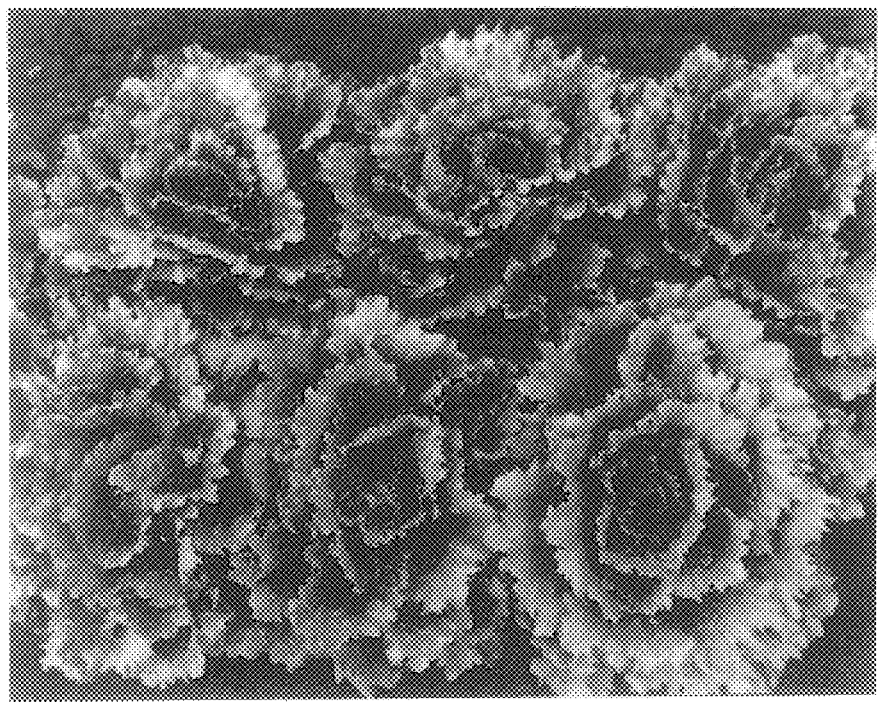
FIG. 2 represents an overhead view of crisphead lettuce treated with 2-chloroethylphosphonic acid.
Figure 3:
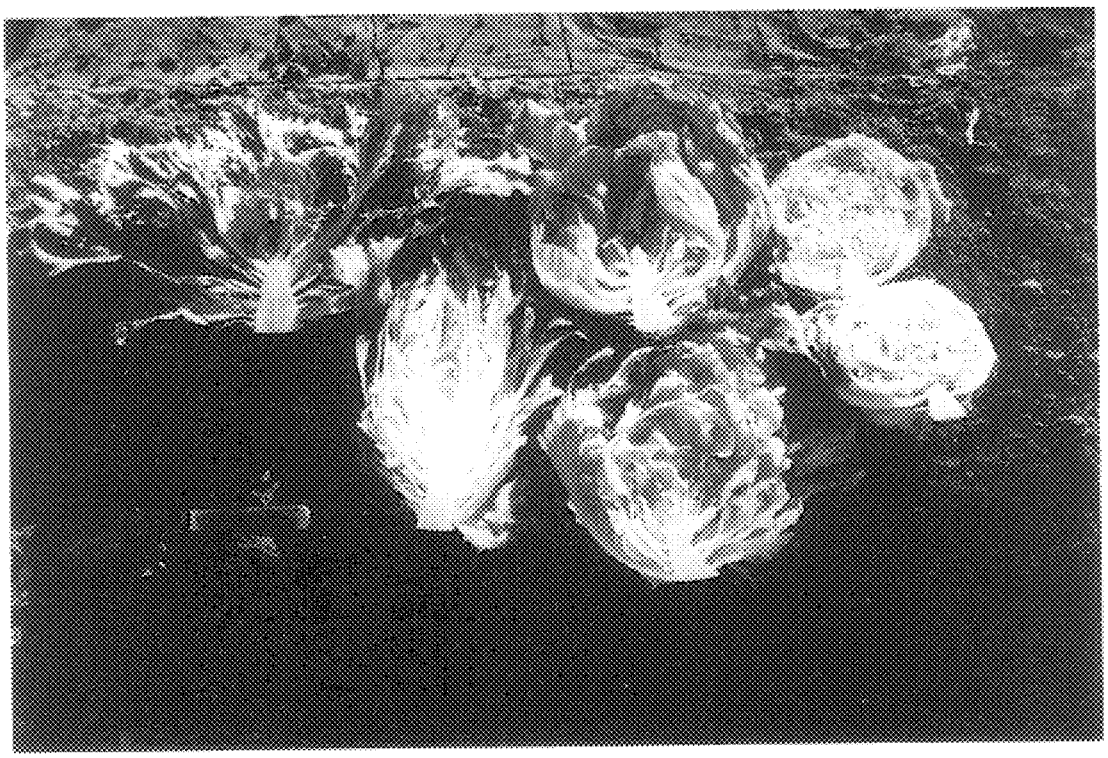
FIG. 3 shows the cross-section of six crisphead lettuces. The four cross-sections on the left were treated with 2-chloroethylphosphonic acid and are indicative of the range of the degree of inhibition of head formation that occurs with treatment. The two plants on the right are untreated crisphead lettuce controls. Though the pigmentation difference cannot be seen in the black and white figures, the four head cross-sections on the left have significantly greener pigmentation than the two controls.

This invention presents a surprising use for catechol or substituted catechol half esters of beta-haloethylphosphonic acids in inhibiting head formation in head-forming lettuce plants. The application of one of these compounds after true leaves have developed results in a decrease in the formation of the head such that interior leaf tissue is more exposed to sunlight. Chlorophyll concentration in the leaves is increased and the resulting leaves have a greater green color which is attractive to the food consumer. It is expected that such increase in chlorophyll formation results in an increase in nutritional value of the plant. The application of these compounds make the lettuce particularly desirable for those preparations in which the leaves are to be used and sold in pre-packaged salads or where the leaves are to be sold separate from the intact plant. The application of catechol or substituted catechol half esters of beta-haloethylphosphonic acids such as 2-chloroethylphosphonic acid may be made to any head-forming lettuce including the crisphead or iceberg types.

Head lettuce or head-forming lettuce refers to those varieties of lettuce in which the leaves grow in a dense rosette. There are generally two subcategories of head lettuce, crisphead (commonly known as iceberg) and butterhead (the Bibb and Boston varieties). Crisphead lettuces are those lettuce plants which in the absence of the treatment proposed herein, form loose or compact heads with leaves that occur after about 10–15 true leaves have formed. The head leaves fold over or otherwise grow over each other such that the inner leaves are shaded from the sun.

The catechol or substituted catechol half ester of beta-haloethylphosphonic acid used in the method of the present invention is soluble in water and can be applied to plants in aqueous solutions composed wholly or partially of water. Partial solutions include those formed of water and, for example, acetone or methylethylketone so long as they are non-toxic to the plant in the final solution. Any liquid medium thus may be used, provided that it is not toxic to the plant. The 2-chloroethylphosphonic acid is marketed commercially by Rhone-Poulenc AG Company, Research Triangle Park, N.C. under the trademark Ethrel®. The preparation of catechol or substituted catechol half esters of beta-haloethylphosphonic acids is disclosed and described in U.S. Pat. Nos. 3,531,549 and 3,551,528, which are both incorporated by reference herein.

The catechol or substituted catechol half ester of beta-haloethylphosphonic acid such as 2-chloroethylphosphonic acid may be applied in any manner such that it is preferably directed to the leaves of the plant. Though the beta-haloethylphosphonic acid described here is generally soluble in water, it may also, if desired, be absorbed onto solid carriers, such as vermiculite, attaclay, talc or other suitable carrier for application via granular vehicle. Application of water-thinned solutions or solids is accomplished using conventional equipment that is well known in the art.

Although the preferred method of application of the compound used in the process of this invention is directly to the foliage, the compound may be applied to the soil in which the plants are growing, such that the compound can be root-absorbed to a sufficient extent so as to result in inhibition of head formation in accordance with this invention.

It is preferred that the compound used in the present invention be applied to crisphead foliage after about 15 to 20 true leaves have formed and, in the case of butterhead foliage after about 10 to 16 true leaves have formed, and before formation of the head. The timing of the application will necessarily vary depending upon the variety of interest and the climate, as is known and appreciated by those in the art. For example, when cold weather varieties are grown in hot weather climates, the heads tend to be looser and the concentration used to inhibit head formation could be less in those cases. Climate conditions may affect how much of the compound actually comes into contact with the plant, as is well known in the field. A single application is generally sufficient to accomplish inhibition of head formation though multiple applications are also acceptable. For example, if a second application is to be utilized, it is preferred that the application be applied about 3 to 10 days after the first application, depending upon growth conditions.

The catechol or substituted catechol half esters of beta-haloethylphosphonic acids such as 2-chloroethylphosphonic acid may be applied to the foliage in an amount sufficient to obtain the desired inhibition of head formation. For example, where Ethrel® is chosen, it is supplied in a 21% solution which is applied in a range of about 50 to about 3000 ml/acre, preferably in a range of about 200 to about 2000 ml/acre and most preferably in a range of about 300 to about 3000 ml/acre. Alternatively, the compounds described here may be applied to an acre at a rate of about 100 to about 2400 ppm, more preferably at a rate of about 200 to about 1200 ppm. Typically on a lettuce crop, one spray application would be made at one of the suggested rates. The total volume of solution sprayed would be at the discretion of the applicator taking into consideration the equipment being used and the weather conditions.

Inhibition of head leaf formation can be readily observed. Typically, the leaves found in the head are in contact with or immediately adjacent the leaves above and below them. Inhibition of head formation results in leaves that do not significantly contact each other and tend toward a more vertical growth orientation.

Typically, crisphead leaf lettuce will have wrapper leaves which are the first leaves to emerge and are those leaves which are not involved in head formation and have a greater green pigmentation. Generally a mature lettuce plant will have about 15 wrapper leaves. If one counts from the outside of the plant toward the center past the wrapper leaves, the next leaves are considered the head leaves. Beginning with the oldest head leaves and working in, the oldest head leaf being designated as head leaf 1, one can count the head leaves of two plants to be compared. Differences between head leaves numbered 5–10 of a plant treated with 2-chloroethylphosphonic acid, for example, compared with head leaves numbered 5–10 of a control plant can be observed. Leaves 5 through 10 that have been treated with 2-chloroethylphosphonic acid will exhibit a substantially more planar and perpendicular growth orientation relative to an unsprayed control. A visible and measurable increase in green pigmentation of the inner leaves can be observed when a corresponding leaf from a treated plant is observed against a control plant of the same variety grown under the same conditions without treatment. See the figures for illustration purposes.

The following example is provided for illustrative reasons and is not to be used to limit the invention as claimed.

EXAMPLES

The following examples are provided for the purposes of illustration and are not to be considered limitations on the invention.

Example 1. A crisphead or butterhead variety of lettuce is planted. When the plants have on average about 15 leaves, a water-based preparation of 2-chloroethylphosphonic acid at 800 ppm is sprayed on the plants with a conventional sprayer in a solution such that it is applied in a final rate of about 60 gallons/acre (about 227 liters).

What is claimed is:

1. A method for inhibiting head formation in a head-forming *Lactuca sativa* plant which comprises applying a catechol or substituted catechol half ester of beta-haloethylphosphonic acid to the plant after leaf formation.

2. The method of claim 1, further wherein the beta-haloethylphosphonic acid is applied after about 15–20 leaves have formed on the plant.

3. The method of claim 1, wherein the beta-haloethylphosphonic acid is 2-chloroethylphosphonic acid.

4. The method of claim 1, further wherein the beta-haloethylphosphonic acid is applied in a soluble form by spray application.

5. The method of claim 1, further wherein the beta-haloethylphosphonic acid is applied at a rate of about 50–3000 ml of a 21% solution per acre.

6. The method of claim 1, wherein the beta-haloethylphosphonic acid is applied in granular form to soil.

7. The method of claim 1, further wherein the beta-haloethylphosphonic acid is applied to the foliage of the plant at a rate of about 100–2000 ml of a 21% solution per acre.

8. The method of claim 1, wherein the plant is crisphead lettuce.

9. The method of claim 1, wherein the plant is butterhead lettuce.

10. A head lettuce variety of *Lactuca sativa* plant in contact with a catechol or substituted catechol half ester of beta-haloethylphosphonic acid.

11. The head lettuce variety of Lactuca sativa plant of claim 10 further wherein the plant is in contact with a 2-chloroethylphosphonic acid preparation.

12. The treated plant of claim 10 in which the plant is a crisphead lettuce plant.

13. The treated plant of claim 10 in which the plant is a butterhead lettuce plant.

* * * * *